United States Patent
Kawabata et al.

(10) Patent No.: US 12,324,706 B2
(45) Date of Patent: Jun. 10, 2025

(54) ULTRASOUND DIAGNOSTIC APPARATUS

(71) Applicant: FUJIFILM Healthcare Corporation, Chiba (JP)

(72) Inventors: Kenichi Kawabata, Chiba (JP); Hideki Yoshikawa, Chiba (JP); Noriaki Inoue, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 43 days.

(21) Appl. No.: 18/494,761

(22) Filed: Oct. 25, 2023

(65) Prior Publication Data

US 2024/0138815 A1 May 2, 2024

(30) Foreign Application Priority Data

Oct. 27, 2022 (JP) .................................. 2022-172684

(51) Int. Cl.
A61B 8/00 (2006.01)

(52) U.S. Cl.
CPC .............. *A61B 8/485* (2013.01); *A61B 8/463* (2013.01); *A61B 8/54* (2013.01)

(58) Field of Classification Search
CPC ........... A61B 8/485; A61B 8/463; A61B 8/54; A61B 8/461; A61B 8/469; A61B 8/5207; A61B 8/5246; A61B 8/5269; A61B 8/44; A61B 8/5215; G16H 30/20
See application file for complete search history.

(56) References Cited

U.S. PATENT DOCUMENTS

| | | | | |
|---|---|---|---|---|
| 6,508,768 B1* | 1/2003 | Hall | ..................... | G01S 7/52061 600/443 |
| 6,558,324 B1* | 5/2003 | Von Behren | ............. | A61B 8/08 600/443 |
| 8,469,891 B2* | 6/2013 | Maleke | .................. | A61B 5/055 73/602 |
| 9,066,679 B2* | 6/2015 | Beach | ....................... | A61B 8/08 |
| 9,603,583 B2* | 3/2017 | Choi | ....................... | A61B 8/485 |

(Continued)

FOREIGN PATENT DOCUMENTS

| | | |
|---|---|---|
| JP | 2015198843 | 11/2015 |
| JP | 2016506846 | 3/2016 |
| JP | 2017221512 | 12/2017 |

*Primary Examiner* — Sanjay Cattungal
(74) *Attorney, Agent, or Firm* — JCIPRNET

(57) ABSTRACT

A push wave transmission unit transmits a push wave to a biological tissue of a subject. A tracking wave transmission/reception unit transmits a tracking wave to the biological tissue and receives a reflected ultrasound wave reflected by the biological tissue. An elasticity analysis unit measures a propagation velocity of a shear wave generated in the biological tissue by the push wave and measures an elastic property of the biological tissue based on the propagation velocity, and measures the propagation velocity of the shear wave based on a measurement signal obtained by the reflected ultrasound wave received by the tracking wave transmission/reception unit. A controller determines whether to re-measure the elastic property according to an unnecessary component included in the measurement signal. When determining to re-measure the elastic property, the ultrasound diagnostic apparatus re-measures the elastic property by changing an acoustic property of the push wave according to the unnecessary component.

10 Claims, 12 Drawing Sheets

(56) References Cited

U.S. PATENT DOCUMENTS

| | | | |
|---|---|---|---|
| 9,726,647 B2* | 8/2017 | Walker | G01N 29/4472 |
| 10,342,514 B2* | 7/2019 | Kanayama | A61B 8/5207 |
| 10,856,849 B2 | 12/2020 | Toji | |
| 11,529,121 B2 | 12/2022 | Sandrin et al. | |
| 2009/0056453 A1* | 3/2009 | McAleavey | A61B 8/5207 |
| | | | 73/597 |
| 2009/0270730 A1* | 10/2009 | Azuma | G01S 7/52042 |
| | | | 600/443 |
| 2009/0292205 A1* | 11/2009 | Osaka | G01S 7/52042 |
| | | | 600/443 |
| 2009/0304246 A1* | 12/2009 | Walker | G01S 15/8979 |
| | | | 382/128 |
| 2011/0263978 A1* | 10/2011 | Chen | A61B 8/485 |
| | | | 600/438 |
| 2012/0253194 A1 | 10/2012 | Tamura | |
| 2013/0102932 A1* | 4/2013 | Cain | A61N 7/02 |
| | | | 601/2 |
| 2013/0211253 A1* | 8/2013 | Hsu | A61B 8/485 |
| | | | 600/438 |
| 2013/0218012 A1* | 8/2013 | Specht | A61B 8/4444 |
| | | | 367/7 |
| 2014/0064021 A1* | 3/2014 | Nagae | G01S 7/52047 |
| | | | 367/7 |
| 2014/0064022 A1* | 3/2014 | Nagae | G01S 7/52046 |
| | | | 367/7 |
| 2014/0064023 A1* | 3/2014 | Nagae | G01S 7/52063 |
| | | | 367/7 |
| 2014/0276058 A1* | 9/2014 | Fan | A61B 5/4872 |
| | | | 600/442 |
| 2014/0330122 A1* | 11/2014 | Baghani | A61B 8/463 |
| | | | 600/438 |
| 2015/0133783 A1* | 5/2015 | Tabaru | A61B 8/485 |
| | | | 600/438 |
| 2015/0148673 A1* | 5/2015 | Yoshikawa | A61B 8/5207 |
| | | | 600/438 |
| 2015/0164476 A1* | 6/2015 | Kong | G01S 7/52022 |
| | | | 600/438 |
| 2015/0182122 A1* | 7/2015 | Bamber | G01S 7/52022 |
| | | | 600/407 |
| 2015/0192547 A1* | 7/2015 | Lee | A61B 8/06 |
| | | | 73/641 |
| 2015/0272547 A1* | 10/2015 | Freiburger | A61B 8/52 |
| | | | 600/438 |
| 2015/0320394 A1* | 11/2015 | Arnal | A61B 8/485 |
| | | | 600/438 |
| 2016/0089113 A1* | 3/2016 | Choi | G01S 15/8979 |
| | | | 600/438 |
| 2016/0128674 A1* | 5/2016 | Shin | A61B 6/5247 |
| | | | 600/436 |
| 2016/0327525 A1* | 11/2016 | Li | A61B 8/485 |
| 2017/0112471 A1* | 4/2017 | Toji | A61B 8/4254 |
| 2017/0340310 A1* | 11/2017 | Carlini | G01S 7/52085 |
| 2017/0347990 A1* | 12/2017 | Watanabe | G01S 7/52022 |
| 2017/0360408 A1* | 12/2017 | Toji | G01S 7/52017 |
| 2018/0296190 A1* | 10/2018 | Susumu | A61B 8/5269 |
| 2019/0183461 A1* | 6/2019 | Sonoyama | G01S 7/52042 |
| 2020/0060654 A1* | 2/2020 | Nguyen | G01S 7/52042 |
| 2023/0044531 A1* | 2/2023 | Etaix | G01N 29/07 |

* cited by examiner

ULTRASOUND DIAGNOSTIC APPARATUS

CROSS-REFERENCE TO RELATED APPLICATION

This application claims the priority benefits of Japanese application no. 2022-172684, filed on Oct. 27, 2022. The entirety of the above-mentioned patent application is hereby incorporated by reference herein and made a part of this specification.

BACKGROUND

1. Technical Field

The disclosure relates to an ultrasound diagnostic apparatus, and more particularly to an apparatus that measures an elastic property of a biological tissue.

2. Description of the Related Art

There is an ultrasound diagnostic apparatus that generates a shear wave in a biological tissue of a subject, measures a propagation velocity of the shear wave, and measures an elastic property of the biological tissue based on the propagation velocity of the shear wave. In this ultrasound diagnostic apparatus, a push wave is transmitted from an ultrasound oscillator or the like to the biological tissue, and the shear wave is excited to the biological tissue by the push wave. By measuring the displacement of each point of the biological tissue due to the shear wave by transmitting and receiving ultrasound wave, the propagation velocity of the shear wave is measured, and the elastic property of the biological tissue is measured based on the propagation velocity of the shear wave.

In JP2017-221512A, JP2016-506846A, and JP2015-198843A, an ultrasound diagnostic apparatus that measures an elastic property of a biological tissue is described. JP2017-221512A describes that a reliability degree of data obtained by measuring a wave surface position of the shear wave is evaluated, and data in which the reliability degree does not satisfy a predetermined condition is interpolated by other data. JP2016-506846A describes that mechanical pulses (push waves) having different frequencies are transmitted to the biological tissue at different timings. JP2015-198843A describes the ultrasound diagnostic apparatus that excites a shear wave in a tissue of a subject by applying pulse oscillation to a probe by a movement of a hand of a user. In this ultrasound diagnostic apparatus, an ultrasound wave is transmitted and received by the probe, a propagation velocity distribution of the shear wave in the biological tissue is measured based on the ultrasound wave received by the probe, and an elastic modulus distribution is further measured.

A measurement signal acquired for measuring the propagation velocity of the shear wave includes unnecessary components, such as a noise component and a reflected wave component. In a case in which the unnecessary component is large, an error occurs in a measured value. The magnitude of the unnecessary component is determined by a physical property of the biological tissue and an acoustic property of the push wave. In a case in which the acoustic property of the push wave is not appropriate with respect to the physical property of the biological tissue, a measurement error of the elastic property may be large.

SUMMARY

The disclosure appropriately sets an acoustic property of a push wave for measuring an elastic property according to a physical property of a biological tissue.

An aspect of the disclosure relates to an ultrasound diagnostic apparatus comprising: a push wave transmission unit that transmits a push wave to a biological tissue; a tracking wave transmission/reception unit that transmits a tracking wave to the biological tissue and receives a reflected ultrasound wave that is reflected by the biological tissue; an elasticity analysis unit that measures a propagation velocity of a shear wave generated in the biological tissue by the push wave and measures an elastic property of the biological tissue based on the propagation velocity, the elasticity analysis unit measuring the propagation velocity based on a measurement signal obtained by the reflected ultrasound wave received by the tracking wave transmission/reception unit; and a controller that determines whether or not to re-measure the elastic property according to an unnecessary component included in the measurement signal, in which, in a case in which it is determined to re-measure the elastic property, the ultrasound diagnostic apparatus re-measures the elastic property by changing an acoustic property of the push wave according to the unnecessary component included in the measurement signal.

It is desirable that the controller determines whether or not to re-measure the elastic property based on a noise component as the unnecessary component included in the measurement signal.

It is desirable that the controller determines whether or not to re-measure the elastic property based on a reflected wave component as the unnecessary component included in the measurement signal.

In addition, another aspect of the disclosure relates to an ultrasound diagnostic apparatus comprising: a push wave transmission unit that transmits a push wave to a biological tissue; a tracking wave transmission/reception unit that transmits a tracking wave to the biological tissue and receives a reflected ultrasound wave that is reflected by the biological tissue; an elasticity analysis unit that measures a propagation velocity of a shear wave generated in the biological tissue by the push wave and measures an elastic property of the biological tissue based on the propagation velocity, the elasticity analysis unit measuring the propagation velocity based on a measurement signal obtained by the reflected ultrasound wave received by the tracking wave transmission/reception unit; and a display processing unit that displays an elasticity image based on the elastic property, in which the ultrasound diagnostic apparatus re-measures the elastic property by changing an acoustic property of the push wave according to an operation of a user performed in a case in which the elasticity image is displayed.

It is desirable that, in a case in which a ratio of magnitude of a shear wave signal component to a noise component included in the measurement signal is less than a predetermined threshold value, in re-measurement, the push wave transmission unit makes a wave train length of the push wave longer than in first-measurement of the elastic property or increases the number of times of transmission of the push wave for each measurement.

It is desirable that, in a case in which a degree of separation between a shear wave signal component and a reflected wave component included in the measurement signal is less than a predetermined threshold value, in re-measurement, the push wave transmission unit makes a wave train length of the push wave shorter than in first-measurement of the elastic property or decreases the number of times of transmission of the push wave for each measurement.

It is desirable that the ultrasound diagnostic apparatus further comprises an image combining unit that generates ultrasound image data of the biological tissue based on the measurement signal, and generates composite image data indicating a composite image in which a re-measurement image based on the ultrasound image data generated in re-measurement of the elastic property is superimposed on a first-measurement image based on the ultrasound image data generated in first-measurement of the elastic property, in which the composite image is an image in which a mixing process is performed on the first-measurement image and the re-measurement image, and the mixing process is a process of weighting and combining a pixel value of the first-measurement image and a pixel value of the re-measurement image according to a position of a pixel.

In addition, still another aspect of the disclosure relates to an ultrasound diagnostic apparatus comprising: a push wave transmission unit that transmits a plurality of types of push waves having different acoustic properties to a biological tissue; a tracking wave transmission/reception unit that transmits a tracking wave to the biological tissue and receives a reflected ultrasound wave that is reflected by the biological tissue; an elasticity analysis unit that measures a propagation velocity of a shear wave generated in the biological tissue by the push wave and measures an elastic property of the biological tissue based on the propagation velocity, the elasticity analysis unit measuring the propagation velocity based on a measurement signal obtained by the reflected ultrasound wave received by the tracking wave transmission/reception unit; and a controller that decides an elastic property having higher reliability out of a first elastic property obtained for one of the plurality of types of push waves and a second elastic property obtained for the other of the plurality of types of push waves, as a finally obtained elastic property, in which the reliability is decided based on an unnecessary component included in the measurement signal.

According to the aspects of the disclosure, it is possible to appropriately set the acoustic property of the push wave for measuring the elastic property according to the physical property of the biological tissue.

DESCRIPTION OF THE EMBODIMENTS

Figure 1:
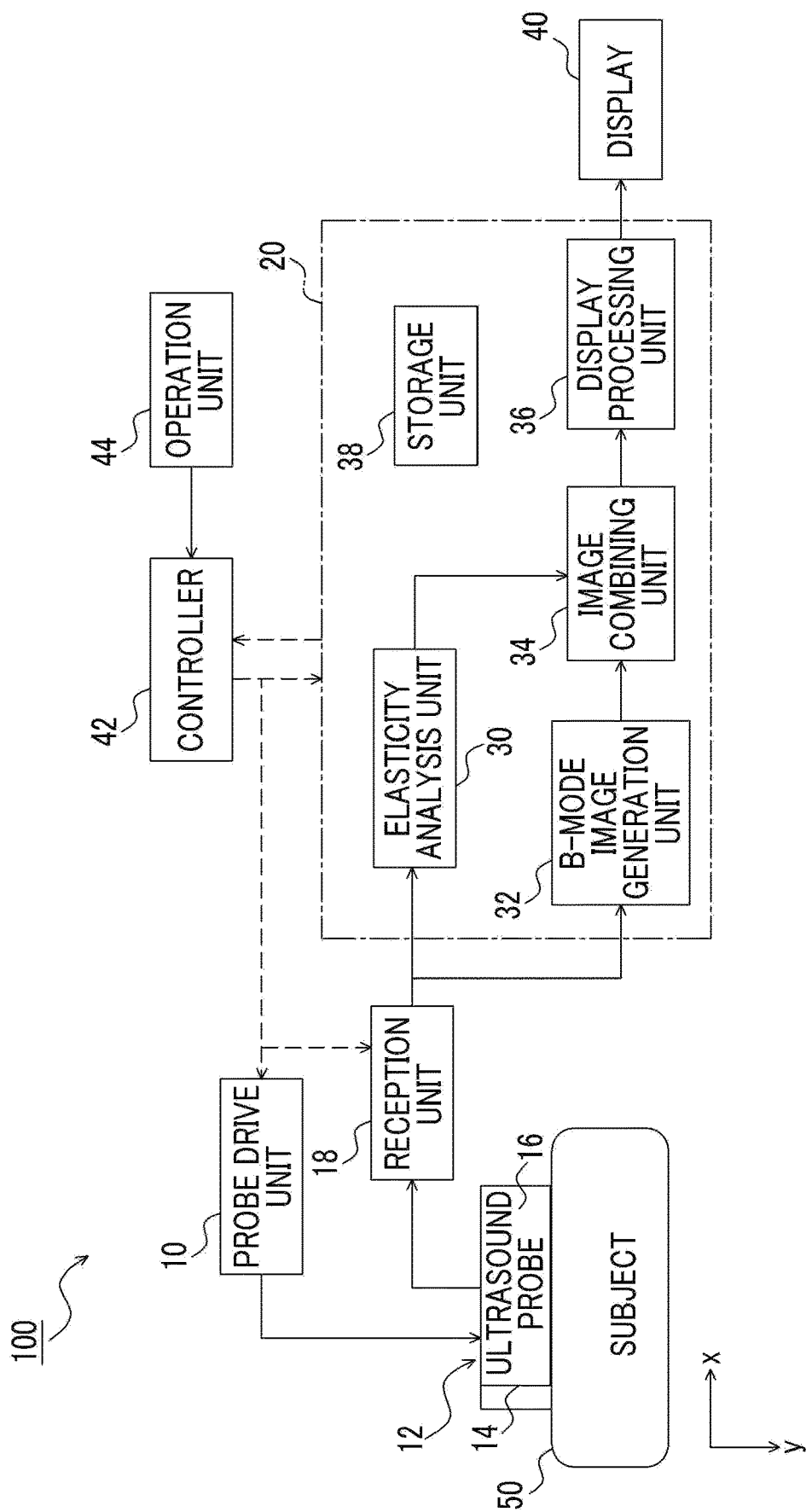
FIG. 1 is a diagram showing a configuration of an ultrasound diagnostic apparatus.

An embodiment of the disclosure will be described with reference to each of the drawings. The same components shown in a plurality of drawings are designated by the same reference numerals, and the description thereof will be simplified.

FIG. 1 shows a configuration of an ultrasound diagnostic apparatus 100 according to the embodiment of the disclosure. The ultrasound diagnostic apparatus 100 comprises a probe drive unit 10, an ultrasound probe 12, a reception unit 18, an information processing unit 20, a display (display device) 40, a controller 42, and an operation unit 44. The operation unit 44 may comprise a button, a lever, a keyboard, a mouse, and the like. The operation unit 44 may be a touch panel provided on the display 40.

The information processing unit 20 comprises an elasticity analysis unit 30, a B-mode image generation unit 32, an image combining unit 34, a display processing unit 36, and a storage unit 38. The information processing unit 20 and the controller 42 may be configured of a processor that executes a program. The information processing unit 20 may configure each component (elasticity analysis unit 30, B-mode image generation unit 32, image combining unit 34, and display processing unit 36) by executing the program. Each component may read data stored in the storage unit 38, may execute an operation, and may store the data obtained as a result of the operation in the storage unit 38. The controller 42 may control the probe drive unit 10, the reception unit 18, and the information processing unit 20 according to an operation of the operation unit 44 by a user.

The ultrasound probe 12 comprises a push wave transmission unit 14 and a tracking wave transmission/reception unit 16. The probe drive unit 10 outputs a push wave drive signal and a transmission signal, respectively, as signals for generating ultrasound waves from the push wave transmission unit 14 and the tracking wave transmission/reception unit 16. The push wave transmission unit 14 transmits a push wave to a subject 50 according to the push wave drive signal output from the probe drive unit 10, and excites a shear wave to the subject 50. The push wave transmission unit 14 may converge the push waves to a focal point determined in the subject 50.

The tracking wave transmission/reception unit 16 transmits a tracking wave as an ultrasound wave for observing a state of a biological tissue of the subject 50 or a propagation state of the shear wave based on the transmission signal output from the probe drive unit 10. The tracking wave transmission/reception unit 16 receives a reflected ultrasound wave generated by being reflected in the subject 50.

The tracking wave transmission/reception unit 16 comprises a plurality of ultrasound oscillators. The probe drive unit 10 may adjust a delay time of the transmission signal to be output to each ultrasound oscillator, and may transmit planar waves as the tracking waves from the plurality of ultrasound oscillators to the subject 50. Each ultrasound oscillator receives the reflected ultrasound wave generated by being reflected in the subject 50, converts the reflected ultrasound wave into a reception signal which is an electrical signal, and outputs the reception signal to the reception unit 18.

The reception unit 18 performs a combining process such as phasing addition on the reception signal output from each ultrasound oscillator to generate a plurality of y-axis direction received beam data. These plurality of y-axis direction received beam data correspond to a plurality of received beams arranged in an x-axis direction toward a depth direction (y-axis direction) of the subject 50. The reception unit 18 generates frame data arranged on a time axis based on the plurality of y-axis direction received beam data, and outputs the frame data to the elasticity analysis unit 30 and the B-mode image generation unit 32.

Figure 2:
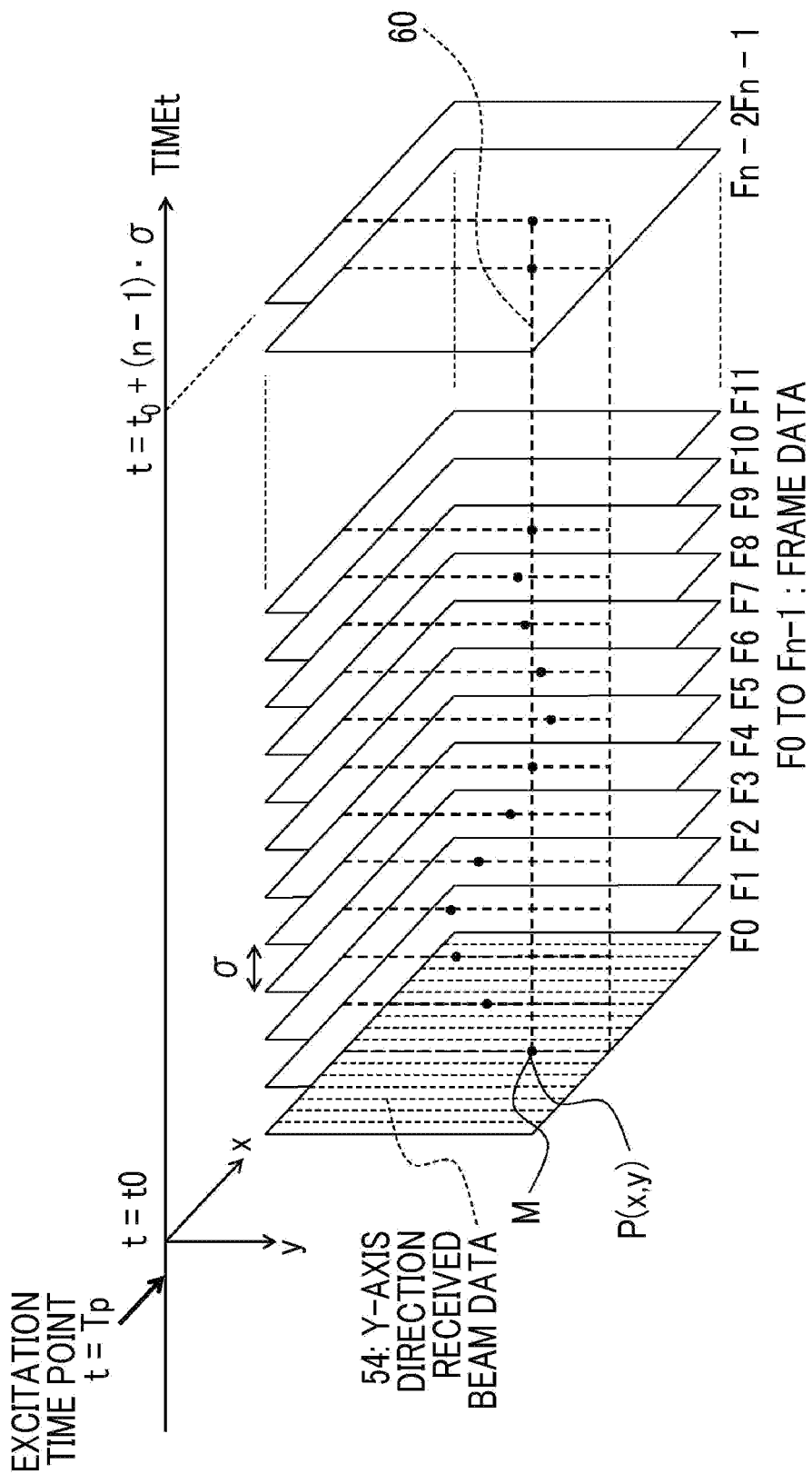
FIG. 2 is a diagram conceptually showing a plurality of frame data generated by a reception unit.

FIG. 2 conceptually shows a plurality of frame data generated by the reception unit 18. FIG. 2, shows an example in which n frame data F0 to Fn−1 are generated at an interval of a time δ between a reference time point t0 after an excitation time point t=Tp at which the push wave is transmitted and a time t0+(n−1)·δ. Each frame data includes a plurality of y-axis direction received beam data 54 corresponding to the plurality of received beams arranged in the x-axis direction.

An xy coordinate is associated with each frame data. That is, one y-axis direction received beam data 54 is associated with the x-coordinate of the corresponding received beam. In addition, a time axis t' of one y-axis direction received beam data 54 is associated with the y-coordinate. Here, in a case in which a velocity of the ultrasound wave in the biological tissue of the subject 50 is denoted by c, there is a relationship of $y=c \cdot t'/2$. The data corresponding to the measurement point P (x, y) in one frame data indicates the intensity of the reflected ultrasound wave at the measurement point P (x, y).

In addition, FIG. 2 conceptually shows a state in which a tissue particle M constituting the biological tissue of the subject 50 is displaced in the y-axis direction with the passage of time due to the shear wave and oscillates. The y-axis direction displacement at the measurement point P (x, y) is the y-axis direction displacement with respect to a straight line 60 perpendicular to an xy plane passing through the measurement point P (x, y).

The elasticity analysis unit 30 measures an elastic property of the biological tissue based on the following processes. That is, the elasticity analysis unit 30 obtains an elastic modulus distribution on the xy plane based on the following processes (i) to (iii).
  (i) The shear wave on the xy plane is detected for each of the plurality of frame data arranged on the time axis.
  (ii) The time required for the shear wave to propagate a certain distance is obtained for each point P on the xy plane to obtain a propagation velocity distribution of the shear wave on the xy plane.
  (iii) The elastic modulus distribution on the xy plane is obtained based on the propagation velocity distribution of the shear wave on the xy plane.

The elasticity analysis unit 30 may obtain a y-axis direction propagation velocity distribution of the shear wave on the xy plane by, for example, the following processes. That is, the elasticity analysis unit 30 obtains the displacement in the y-axis direction per time δ based on two frame data adjacent to each other at the time interval δ on the time axis, and obtains y-axis direction velocity components Vy (x, y) and Vy (x, y+Δ) of the oscillation due to the shear wave. However, Vy (x, y+Δ) indicates the y-axis direction velocity component at a position separated from the point (x, y) by A in the y-axis direction.

The elasticity analysis unit 30 obtains time waveforms of the y-axis direction velocity components Vy (x, y) and Vy (x, y+Δ). Further, the elasticity analysis unit 30 obtains a y-axis direction propagation velocity of the shear wave at the measurement point P (x, y) based on the time waveform of the y-axis direction velocity component Vy (x, y) and a movement amount on the time axis of the time waveform of the y-axis direction velocity component Vy (x, y+Δ), and obtains the y-axis direction propagation velocity distribution of the shear wave on the xy plane. The elasticity analysis unit 30 obtains the elastic modulus distribution on the xy plane based on the y-axis direction propagation velocity distribution of the shear wave on the xy plane. The elastic modulus is a value proportional to the square of the propagation velocity, and represents the hardness of the biological tissue.

The elasticity analysis unit 30 generates elasticity image data indicating the elastic modulus distribution on the xy plane, and outputs the elasticity image data to the image combining unit 34. The elasticity image data may be, for example, image data indicating an elasticity image in which a region having a smaller elastic modulus is subjected to a color having a shorter wavelength and a region having a larger elastic modulus is subjected to a color having a longer wavelength.

The elasticity analysis unit 30 may obtain the elastic modulus distribution based on other processes according to the procedures (i) to (iii) described above.

The B-mode image generation unit 32 generates B-mode image data arranged on the time axis based on the frame data arranged on the time axis, and outputs the B-mode image data to the image combining unit 34. The B-mode image data is data indicating an echo image in a tomographic plane into which the planar wave transmitted from the tracking wave transmission/reception unit 16 propagates.

The image combining unit 34 generates a B-mode elasticity image in which the elasticity image is superimposed on the B-mode image corresponding to the same time point based on the elasticity image data and the B-mode image data corresponding to the same time point. This image may be an image obtained by subjecting a B-mode image to the color corresponding to the elastic modulus. The image combining unit 34 outputs the B-mode elasticity image data to the display processing unit 36. The display processing unit 36 converts the B-mode elasticity image data into a video signal, and outputs the video signal to the display 40. The display 40 displays the B-mode elasticity image based on the video signal.

The image combining unit 34 may output only the B-mode image data to the display processing unit 36 and may display only the B-mode image on the display 40 according to the operation of the operation unit 44 by the user. The image combining unit 34 may output only the elasticity image data to the display processing unit 36 and may display only the elasticity image on the display 40 according to the operation of the operation unit 44 by the user.

A position of the focal point of the push waves may be set by the user. The setting of the position of the focal point may be performed, for example, by performing an operation of setting the position of the focal point on the tomographic plane from which the B-mode image is acquired, in a state in which the display processing unit 36 displays the B-mode image on the display 40.

The elastic modulus distribution may be obtained for a region of interest designated by the user. The setting of the region of interest is performed, for example, by performing an operation of setting the region of interest on the tomographic plane from which the B-mode image is acquired, in a state in which the display processing unit 36 displays the B-mode image on the display 40. In this case, the tracking wave transmission/reception unit 16 may transmit and receive the tracking wave only in a region, in which the elastic modulus distribution is acquired, among the regions on the tomographic plane.

Figure 3:
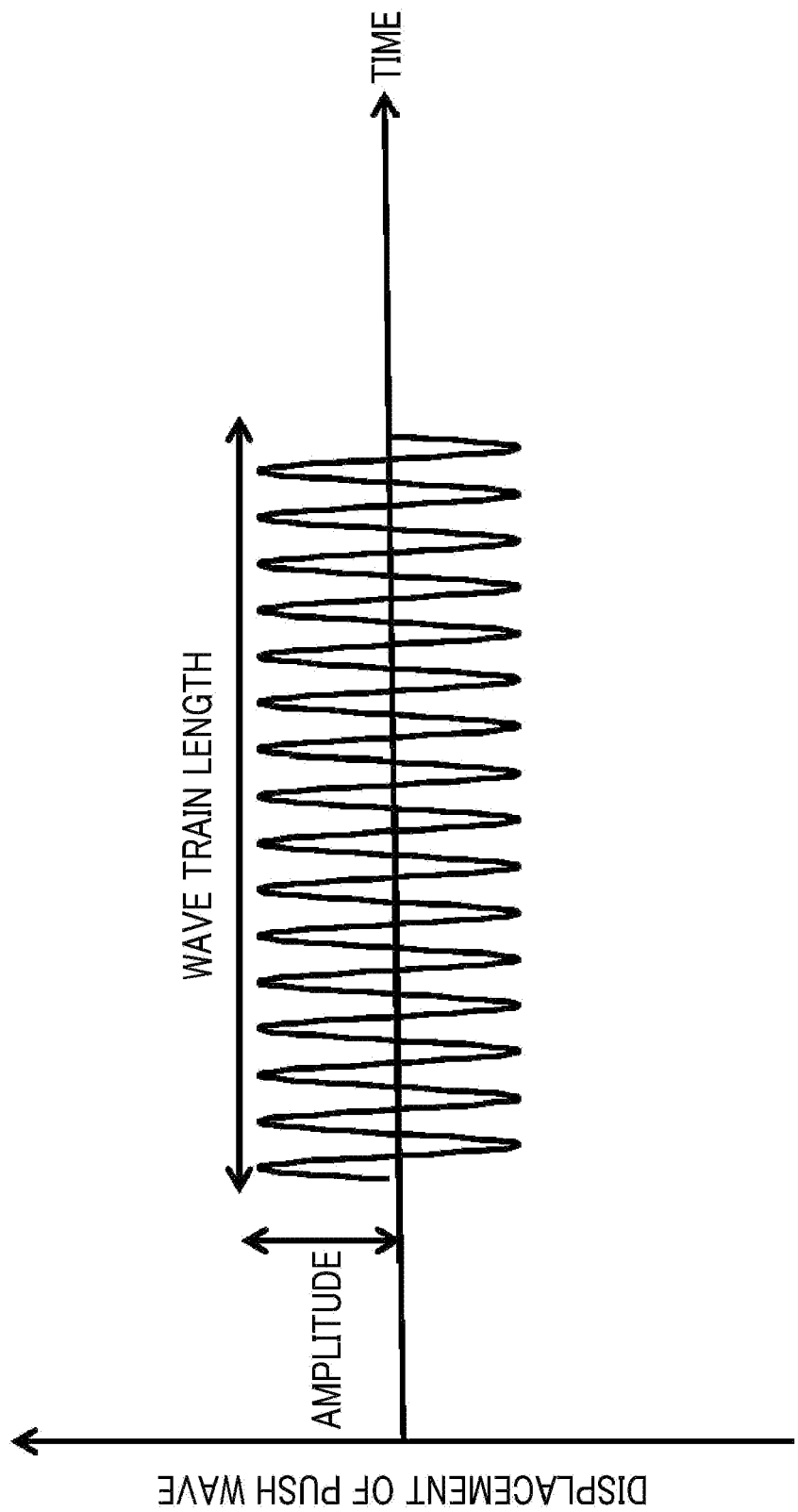
FIG. 3 is a diagram schematically showing a time waveform of a push wave.

An acoustic property of the push wave includes the wave train length and an amplitude. FIG. 3 schematically shows a time waveform of the push wave. A horizontal axis indicates a time, and a vertical axis indicates an instantaneous value of the displacement caused by the push wave. The wave train length indicates the periodicity of the push wave in a case in which the push wave is transmitted once. In a case of acquiring the B-mode elasticity image, the user may set the wave train length and the amplitude of the push wave by operating the operation unit 44. In order to reduce the burden on the biological tissue, the wave train length may be set to various values while the amplitude is maintained invariable at an allowable maximum value. The controller 42 reads each set value of the wave train length and the amplitude from the operation unit 44, and controls the probe drive unit 10 such that the amplitude and the wave train length of the push wave transmitted from the push wave transmission unit 14 are values corresponding to the set values.

Figure 4A:
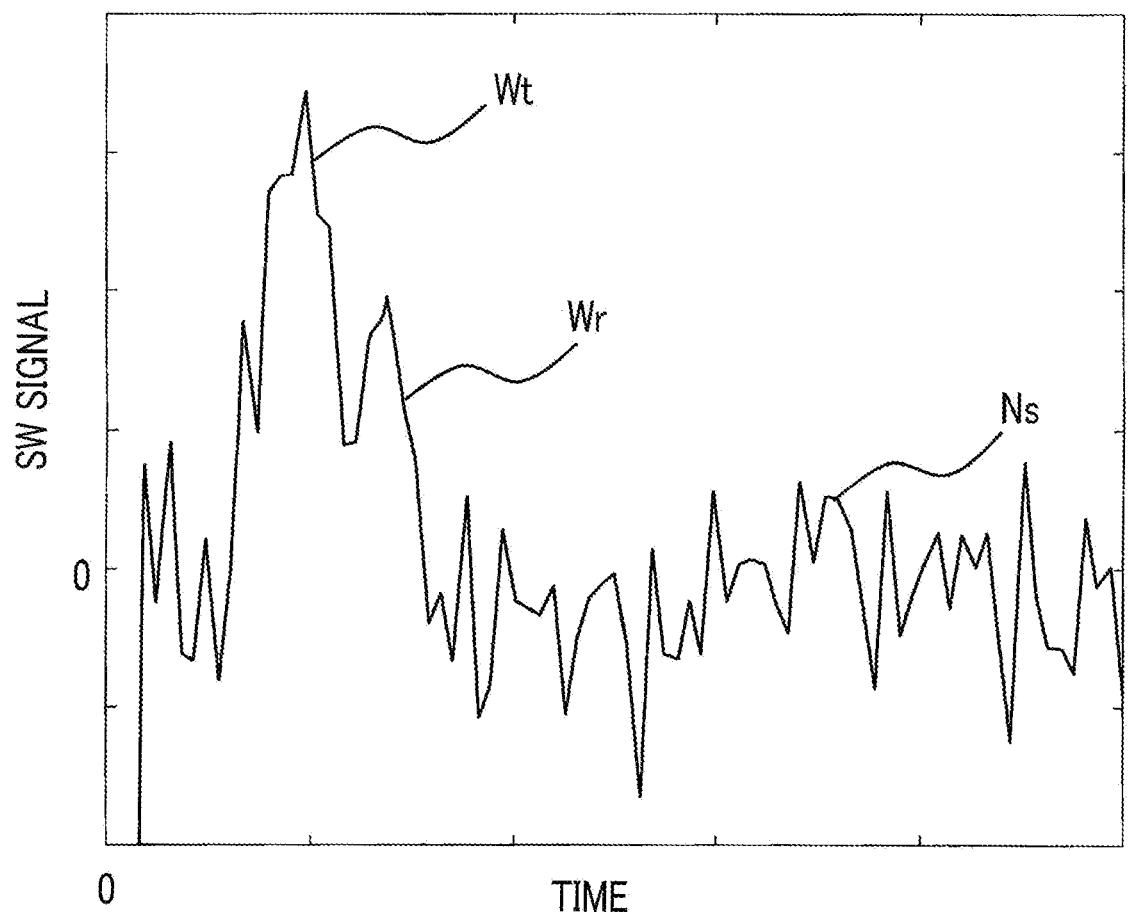
FIG. 4A is a diagram showing a time waveform of a SW signal at a certain measurement point on a tomographic plane.
Figure 4B:
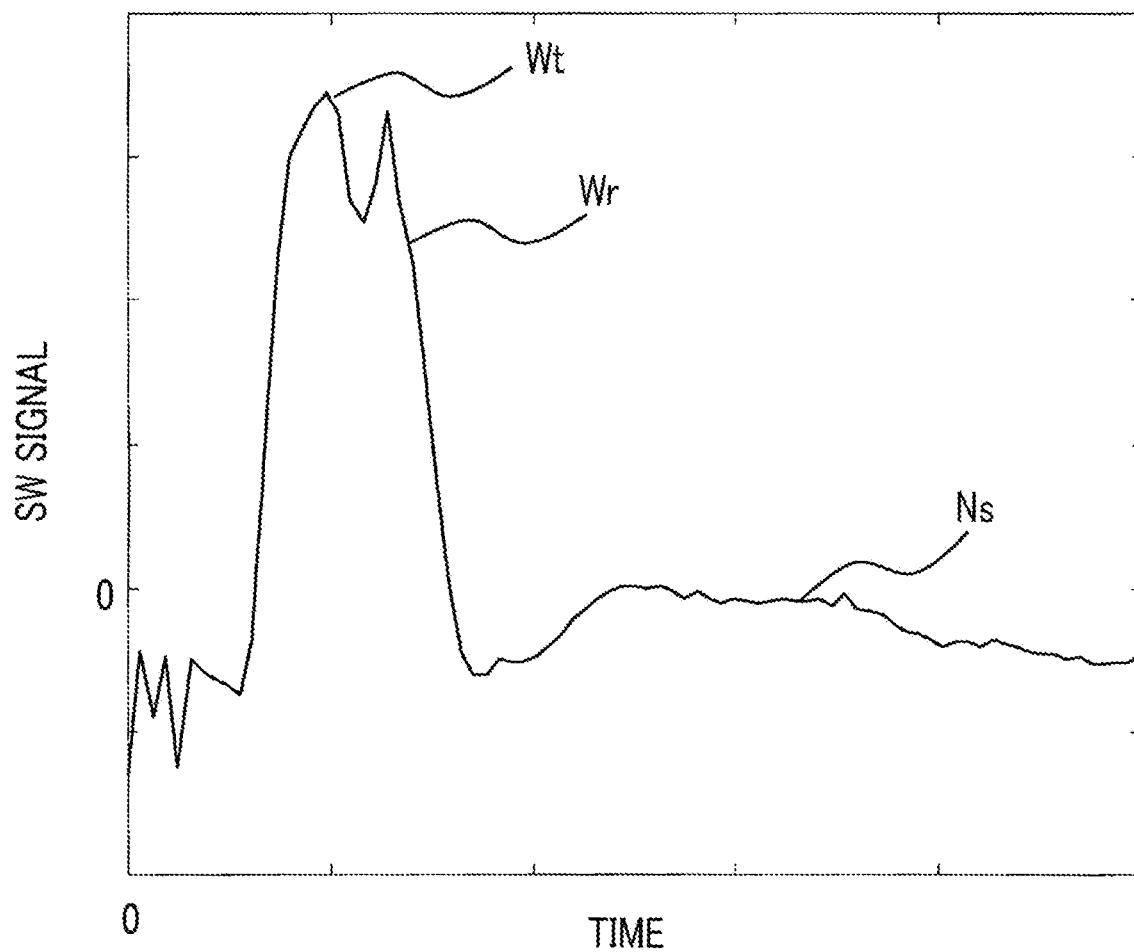
FIG. 4B is a diagram showing a time waveform of the SW signal at a certain measurement point on the tomographic plane.
Figure 4C:
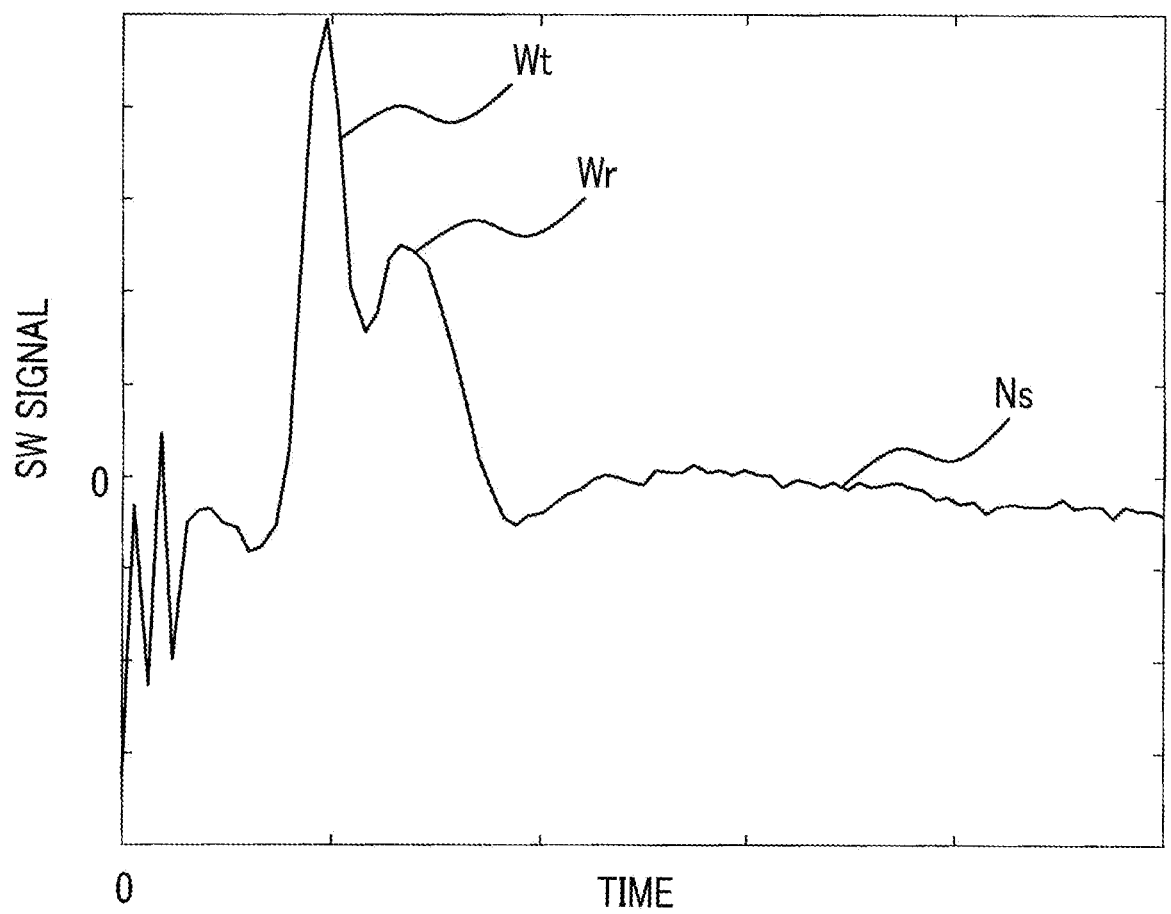
FIG. 4C is a diagram showing a time waveform of the SW signal at a certain measurement point on the tomographic plane.

A traveling wave and a reflected wave of the shear wave propagate to the biological tissue. The reflected wave is generated by the reflection of a part of the traveling waves in a region in which a medium in the biological tissue is discontinuous. The traveling wave contributes to the measurement of the elastic modulus. FIGS. 4A to 4C show the time waveforms of shear wave (SW) signals at a certain measurement point P (x, y) on the tomographic plane under three conditions of the same amplitude and different wave train lengths. A horizontal axis indicates a time, and a vertical axis indicates a value of the shear wave (SW) signal, that is, the displacement of the biological tissue.

The SW signal is a measurement signal for measuring the propagation velocity of the shear wave. The SW signal indicates the displacement of the biological tissue based on the traveling wave and the reflected wave of the shear wave. In addition, a noise component is included in the SW signal. The traveling wave is a shear wave signal component for measuring the propagation velocity of the shear wave, and the reflected wave (reflected wave component) and the noise component are unnecessary components that should not contribute to the measurement of the propagation velocity of the shear wave.

FIG. 4A shows an example in a case in which the wave train length of the push wave is too short. In this example, the displacement due to a traveling wave Wt is not sufficient, and the accuracy of the measured elastic modulus may be decreased due to a noise component Ns. FIG. 4B shows an example in a case in which the wave train length of the push wave is too long. In this example, the traveling wave Wt and a reflected wave Wr may overlap and interfere with each other on the time axis, and a spatial resolution in a case of measuring the elastic modulus may be decreased. FIG. 4C shows an example in a case in which the wave train length of the push wave is appropriate. In this example, the displacement due to the traveling wave is sufficient, and the traveling wave and the reflected wave are separated on the time axis.

Figure 5:
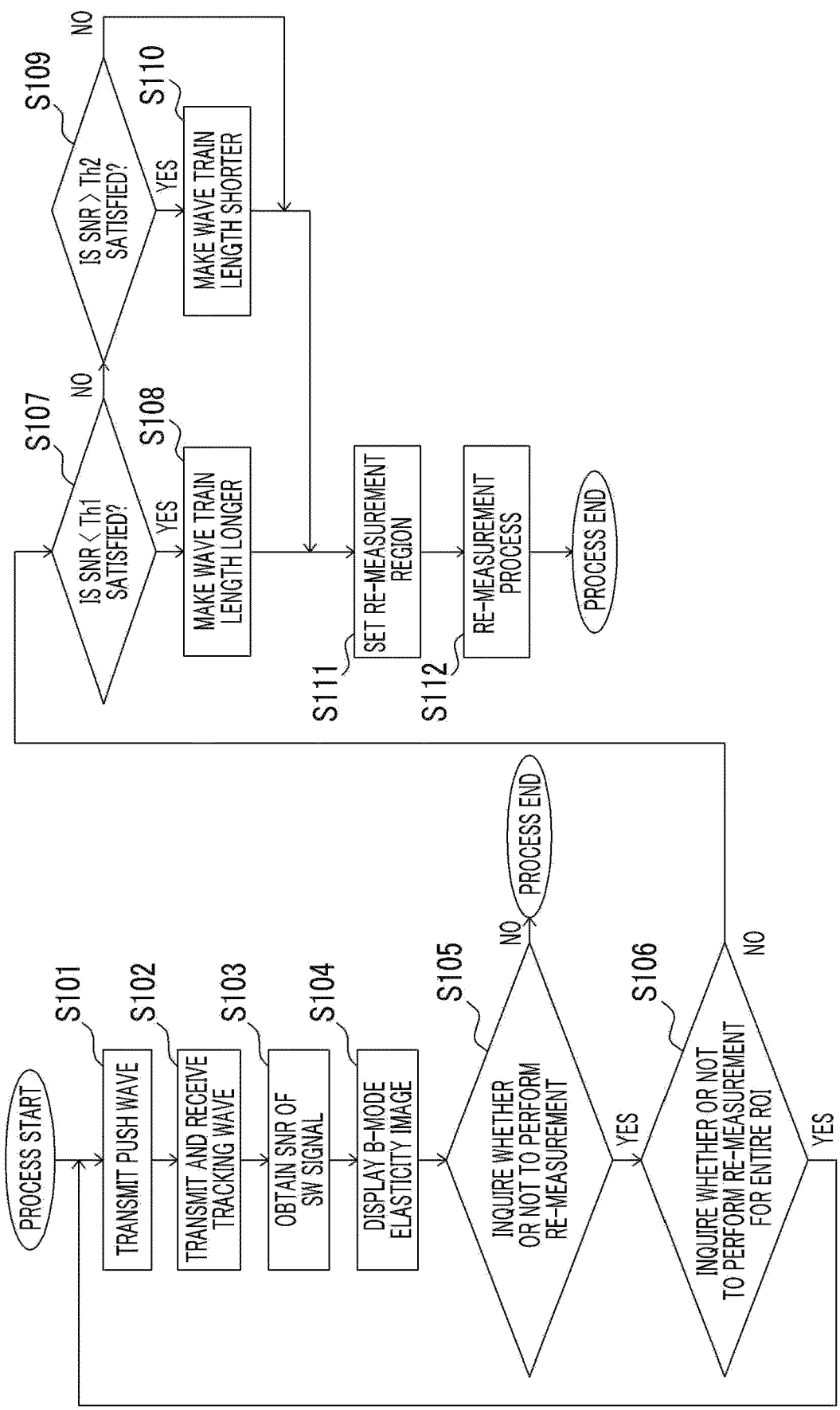
FIG. 5 is a flowchart showing an adjustment process in a case in which a determination of whether or not to change a wave train length is performed based on a ratio of a shear wave signal component to a noise component.

In the ultrasound diagnostic apparatus 100 according to the present embodiment, an adjustment process of adjusting the amplitude and the wave train length of the push wave is executed based on a result of the measurement of the SW signal or the elastic modulus distribution. FIG. 5 shows a flowchart showing the adjustment process.

First, the controller 42 sets a region of interest (denoted by "ROI" in FIGS. 5 to 7, and 10, and ROI is an abbreviation for region of interest) for the tomographic plane of the subject 50 based on the operation of the operation unit 44 by the user. In addition, the controller 42 sets the wave train length and the amplitude of the transmitted push wave to predetermined initial values. Each set value of the wave train length and the amplitude of the push wave may be read from the operation unit 44 according to the operation of the operation unit 44 by the user, and the wave train length and the amplitude of the push wave are set to each set value.

The push wave transmission unit 14 transmits the push wave having the wave train length and the amplitude that are set by the controller 42 (S101). The tracking wave transmission/reception unit 16 transmits the tracking wave to the subject 50, and receives the reflected ultrasound wave generated by the reflection of the tracking wave in the subject 50 (S102).

The tracking wave transmission/reception unit 16 outputs the reception signal from each ultrasound oscillator to the reception unit 18, and the reception unit 18 generates the frame data based on the reception signal output from each ultrasound oscillator. The tracking wave transmission/reception unit 16 repeatedly executes the transmission and the reception of the tracking wave, and the reception unit 18 generates the frame data arranged on the time axis.

The elasticity analysis unit 30 generates the SW signal based on the frame data of a plurality of frames arranged on the time axis. The SW signal may be a signal at the measurement point P (x0, y0) (representative point) represented in the region of interest. The elasticity analysis unit 30 obtains a signal-to-noise ratio (hereinafter, referred to as SNR) for the SW signal (S103). The SNR represents a ratio of the shear wave signal component to the noise component included in the SW signal. In addition, the elasticity analysis unit 30 generates the elasticity image data based on the frame data of the plurality of frames arranged on the time axis, and outputs the elasticity image data to the image combining unit 34.

In the above, the example is shown in which the SNR is obtained from the SW signal at one representative point P (x0, y0). The SNR may be a statistical value of the SNR of the SW signal obtained for each of the plurality (n) of representative points P (x0, y0) to P (xn, yn). Here, examples of the statistical value include an average value, a median value, and a most frequent value.

The B-mode image generation unit 32 generates the B-mode image data based on the frame data output from the reception unit 18, and outputs the B-mode image data to the image combining unit 34. The image combining unit 34 generates the B-mode elasticity image based on the elasticity image data output from the elasticity analysis unit 30 and the B-mode image data output from the B-mode image generation unit 32. The image combining unit 34 outputs the B-mode elasticity image data to the display processing unit 36. The display processing unit 36 displays the B-mode elasticity image on the display 40 (S104).

The display processing unit 36 displays the B-mode elasticity image on the display 40 (S104), and displays inquiry information output from the controller 42 on the display 40 (S105, S106). The inquiry information includes information for inquiring the user whether or not to perform the re-measurement and information for inquiring whether or not to perform the re-measurement for the entire region of interest.

The display processing unit 36 displays the information for inquiring whether or not to perform the re-measurement on the display 40 (S105). In a case in which this information is displayed and the information indicating that the re-measurement is not to be performed is input from the operation unit 44, the ultrasound diagnostic apparatus 100 terminates the measurement process. On the other hand, in a case in which the information indicating that the re-measurement is to be performed is input from the operation unit 44, the display processing unit 36 displays the information for inquiring whether or not to perform the re-measurement for the entire region of interest (ROI) on the display 40 (S106). In a case in which this information is displayed and the information indicating that the re-measurement for the entire region of interest is to be performed is input from the operation unit 44, the controller 42 executes the process of step S101.

On the other hand, in a case in which the information indicating that the re-measurement is to be performed for a part of the region of interest instead of the entire region of interest is input from the operation unit 44, the controller 42 executes control for performing the re-measurement in which the acoustic property of the push wave is changed, as described below. That is, the controller 42 determines whether or not the SNR obtained for the SW signal is less than a threshold value Th1 (S107). In a case in which the SNR is less than the threshold value Th1, the controller 42 sets the wave train length to be longer than the previously set wave train length (S108), and proceeds to the process of step S111. In a case in which the SNR is equal to or larger than the threshold value Th1, the controller 42 determines whether or not the SNR obtained for the SW signal exceeds a threshold value Th2 (S109). In a case in which the SNR exceeds the threshold value Th2, the controller 42 sets the wave train length to be shorter than the previously set wave train length (S110), and proceeds to the process of step S111. In a case in which the SNR is equal to or larger than the threshold value Th1 and equal to or less than the threshold value Th2, the controller 42 proceeds to the process of step S111 while maintaining the wave train length at the previously set length.

The process of step S108 may be a process of setting the wave train length to K times (K is an integer equal to or larger than 2) of the previously set wave train length. In addition, the process of step S110 may be a process of setting the wave train length to 1/J times (J is an integer equal to or larger than 2) of the previously set wave train length.

In step S111, the controller 42 sets a re-measurement region (S107). The setting of the re-measurement region is performed, for example, by performing an operation of setting the re-measurement region on the tomographic plane, in a state in which the display processing unit 36 displays the B-mode image on the display 40. In this case, the display processing unit 36 may display information for instructing the user to set the re-measurement region as a partial region of the region of interest that is previously set on the display 40.

After the re-measurement region is set (S111), the ultrasound diagnostic apparatus 100 executes a re-measurement process (S112) for the re-measurement region. In the re-measurement process, the same process as in steps S101 to S104 is executed for the re-measurement region.

With such a process, the ultrasound diagnostic apparatus 100 re-measures the elastic property according to the operation of the user performed in a case in which the B-mode elasticity image is displayed. That is, after the B-mode elasticity image is displayed on the display 40, the user selects whether or not to perform the measurement again. Further, the user selects whether to perform the re-measurement for the entire region of interest or to perform the re-measurement for a part of the region of interest. Since the setting related to the re-measurement is performed according to the knowledge or the experience of the user, the elastic modulus distribution can be appropriately acquired even in a case in which the determination is difficult only by the operation process by the ultrasound diagnostic apparatus 100.

In addition, with such a process, in a case in which the SNR is less than the threshold value Th1 the accuracy of the measured elastic modulus may be decreased due to the noise component Ns as shown in FIG. 4A, the wave train length is made longer than the previously set length.

In a case in which the SNR is larger than the threshold value Th2, the wave train length is made shorter than the previously set length, and the spatial resolution in a case of measuring the elastic modulus is prevented from being decreased as shown in the example of FIG. 4B.

In a case in which the SNR is equal to or larger than the threshold value Th1 and equal to or less than the threshold value Th2, as shown in the example of FIG. 4C, the displacement due to the traveling wave is sufficient, and the traveling wave and the reflected wave of the shear wave may be separated on the time axis, the wave train length is maintained at the previously set length.

Therefore, with the ultrasound diagnostic apparatus 100 according to the present embodiment, the elastic modulus distribution is obtained for the re-measurement region after an appropriate wave train length is set, so that the elastic modulus distribution is obtained with high accuracy.

Figure 6:
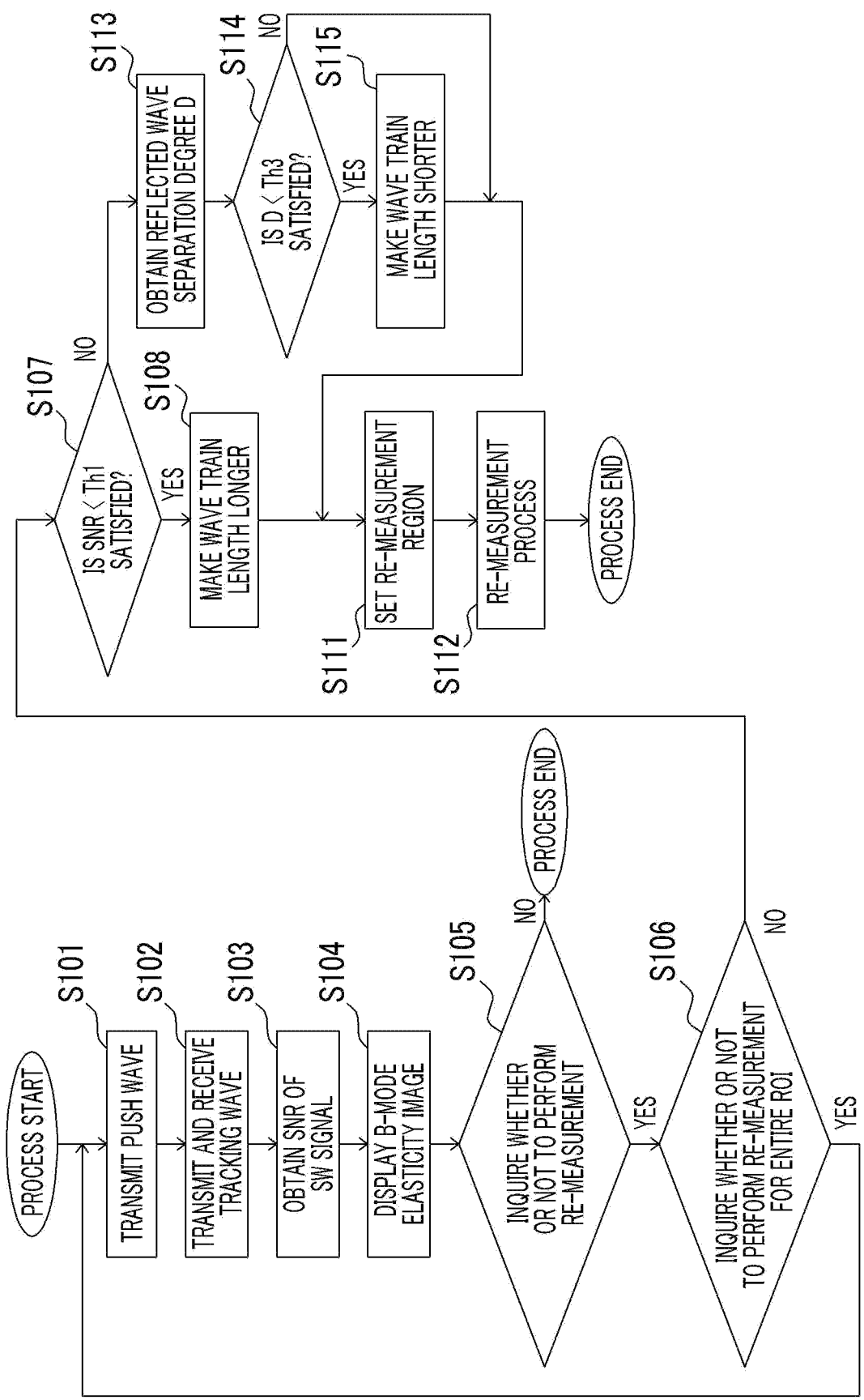
FIG. 6 is a flowchart showing an adjustment process in a case in which a determination of whether or not to change the wave train length is performed based on a degree of separation between a traveling wave and a reflected wave of a shear wave.

In addition, instead of the determination of step S109, a determination of whether or not to make the wave train length shorter may be performed based on a degree of separation between the traveling wave and the reflected wave of the shear wave. FIG. 6 shows a flowchart of the adjustment process executed by the ultrasound diagnostic apparatus 100 in this case. The controller 42 determines whether or not the SNR obtained for the SW signal is less than the threshold value Th1 (S107), and obtains a reflected wave separation degree D based on the B-mode image data and the elasticity image data in a case in which the SNR is equal to or larger than the threshold value Th1 (S113). The reflected wave separation degree D indicates a degree (degree of separation) at which the traveling wave and the reflected wave of the shear wave are separated. The reflected wave separation degree D may be represented by, for example, a degree of approximation between a boundary line of the image indicated by the B-mode image data and a boundary line of the image indicated by the elasticity image.

The controller 42 executes a process of extracting the boundary line of the B-mode image for the B-mode image data, and executes a process of extracting the boundary line of the elasticity image for the elasticity image data. The controller 42 performs a correlation operation on the boundary line of the B-mode image and the boundary line of the elasticity image, and obtains a correlation value (boundary line correlation value) between the boundary line of the B-mode image and the boundary line of the elasticity image as the reflected wave separation degree D.

In addition, the controller 42 may obtain the reflected wave separation degree D by applying the B-mode image data and the elasticity image data to a learning model constructed from training data acquired in advance. The training data may be, for example, data including a plurality of sets of the B-mode image data, tomographic image data, and the boundary line correlation values acquired for various subjects 50 in the past.

The controller 42 determines whether or not the reflected wave separation degree D is less than a predetermined threshold value Th3 (S114). In a case in which the reflected wave separation degree D is less than the predetermined threshold value Th3, the controller 42 sets the wave train length to be shorter than the wave train length previously set (S115), and proceeds to the process of step S111. In a case in which the reflected wave separation degree D is equal to or larger than the threshold value Th3, the controller 42 proceeds to the process of step S111 while maintaining the wave train length at the previously set length.

In the processes shown in FIGS. 5 and 6, the information for inquiring whether or not to perform the re-measurement is displayed on the display 40 in step S105, and the controller 42 executes a process corresponding to the operation in a case in which this information is displayed. Further, in step S106, the information for inquiring whether or not to perform the re-measurement for the entire region of interest is displayed on the display 40, and the controller 42 executes a process corresponding to the operation in a case in which this information is displayed. Instead of the controller 42 executing the process corresponding to the display of the inquiry information, the controller 42 may execute a determination of whether or not to perform the re-measurement and a determination of whether or not to perform the re-measurement for the entire region of interest, based on the process executed by the controller 42 itself.

Figure 7:
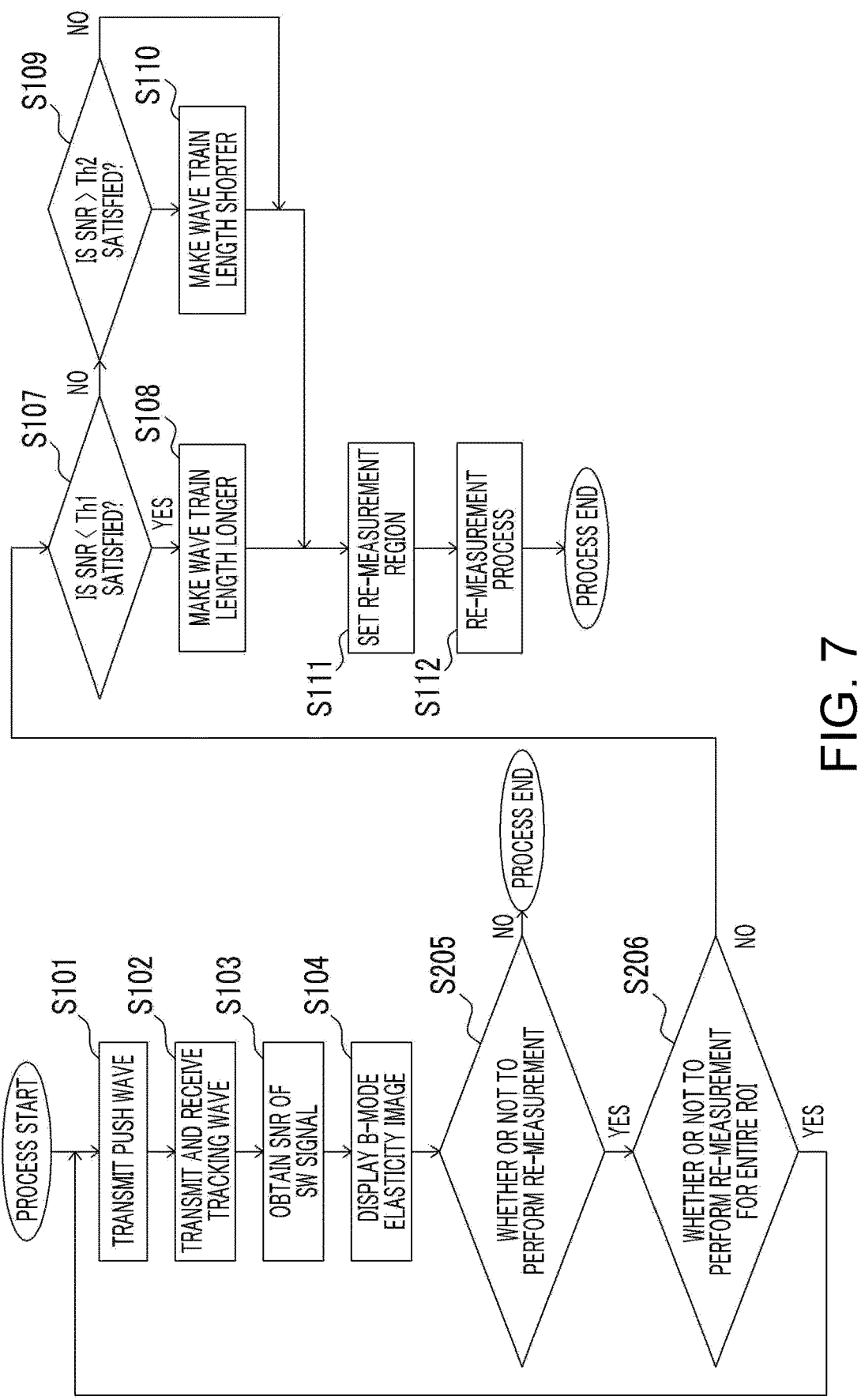
FIG. 7 is a flowchart showing a case in which a controller executes a determination of whether or not to perform re-measurement and a determination of whether or not to perform the re-measurement for an entire region of interest.

FIG. 7 shows a flowchart of such a process. In step S205, the controller 42 determines, for example, whether or not to perform the re-measurement based on the SW signal. For example, in a case in which the SNR of the SW signal is less than a predetermined threshold value Tha, the controller 42 may determine to perform the re-measurement. In addition, the controller 42 may obtain the reflected wave separation degree D, and may determine to perform the re-measurement in a case in which the reflected wave separation degree D is less than a predetermined threshold value Thb. Further, the controller 42 may determine to perform the re-measurement in a case in which the SNR of the SW signal is less than the predetermined threshold value Tha and the reflected wave separation degree D is less than the predetermined threshold value Thb. The controller 42 terminates the process in a case in which it is determined not to perform the re-measurement, and proceeds to the process of step S206 in a case in which it is determined to perform the re-measurement.

In step S206, for example, the controller 42 divides the region of interest into a plurality of sub-regions of interest by N, and obtains a reflected wave separation degree Di (i=1 to N) for each of the sub-regions of interest. Further, in a case in which the number of regions in which the reflected wave separation degree Di is less than a predetermined threshold value Thc is equal to or larger than a predetermined number L, it is determined to perform the re-measurement for the entire region of interest. On the other hand, in a case in which the number of regions in which the reflected wave separation degree Di is less than the predetermined threshold value Thc is less than the predetermined number L, the controller 42 proceeds to the process of step S107 and subsequent steps of performing the re-measurement for the re-measurement region.

Figure 8:
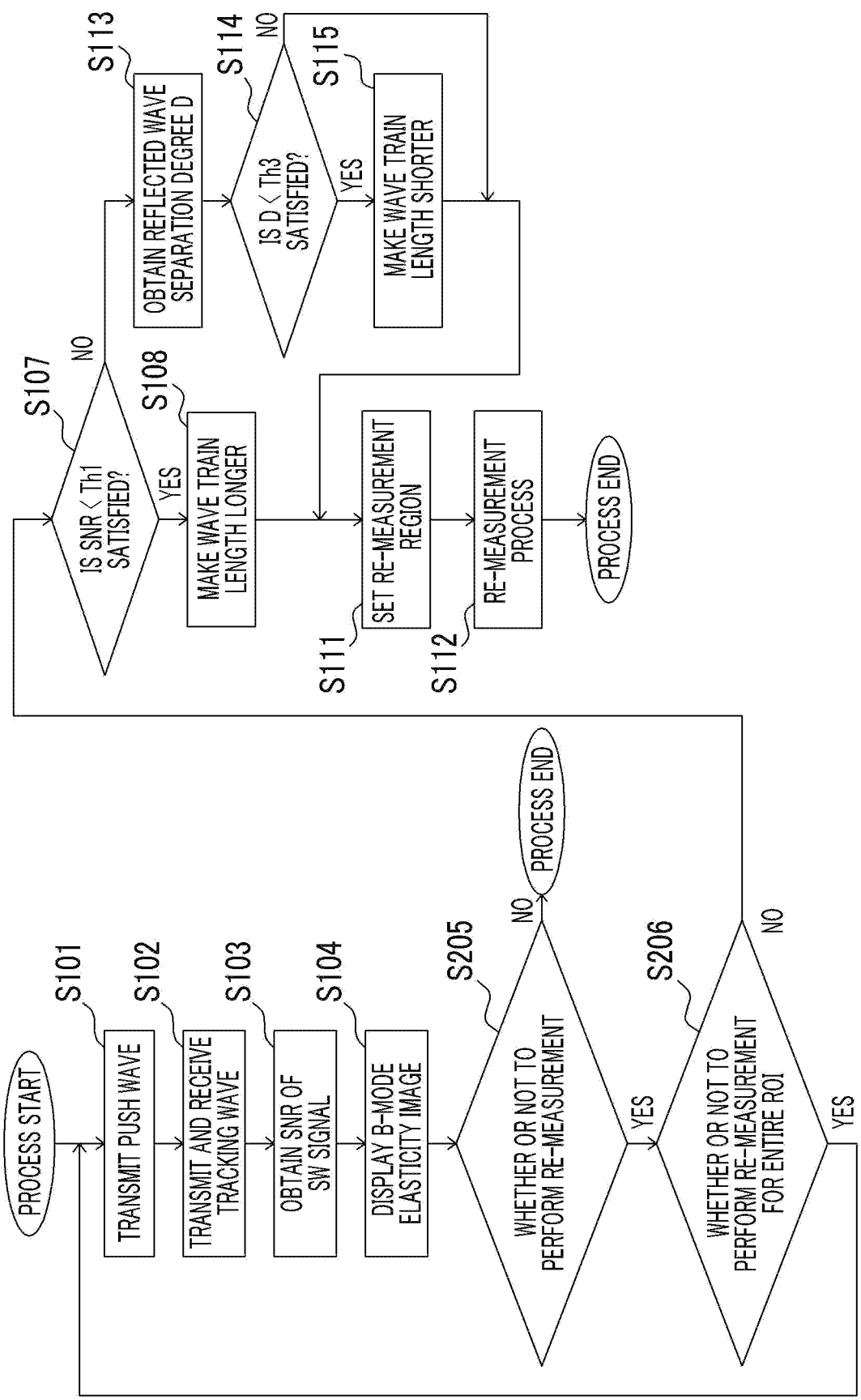
FIG. 8 is a flowchart showing a case in which the controller executes the determination of whether or not to perform the re-measurement and the determination of whether or not to perform the re-measurement for the entire region of interest.

In the process shown in the flowchart of FIG. 8, steps S105 and S106 shown in FIG. 6 are replaced with processes (S205 and S206) executed by the controller 42.

The process of step S101 shown in FIGS. 5 to 8 may be a process of transmitting the push wave having a predetermined wave train length within a predetermined number of times within a certain time. In this case, instead of making the wave train length longer in step S108, a process of executing the re-measurement process (S112) may be executed by maintaining the wave train length invariable and increasing the number of times of transmission of the push wave within the certain time as compared to the previous number of times of transmission of the push wave. The number of times of transmission of the push wave within the certain time is the number of times of transmission for each measurement. In addition, instead of making the wave train length shorter in step S110 or S115, the controller 42 may execute a process of executing the re-measurement process (S112) by maintaining the wave train length invariable and decreasing the number of times of transmission of the push wave within the certain time as compared to the previous number of times of transmission of the push wave.

Next, the image displayed on the display 40 in the re-measurement process (S112) shown in FIGS. 5 to 8 will be described. In the re-measurement process, the controller 42 causes the image combining unit 34 to execute a process of displaying a composite image in which the B-mode elasticity image is superimposed on the B-mode elasticity image (hereinafter, referred to as re-measurement image) generated for the re-measurement region.

Figure 9:
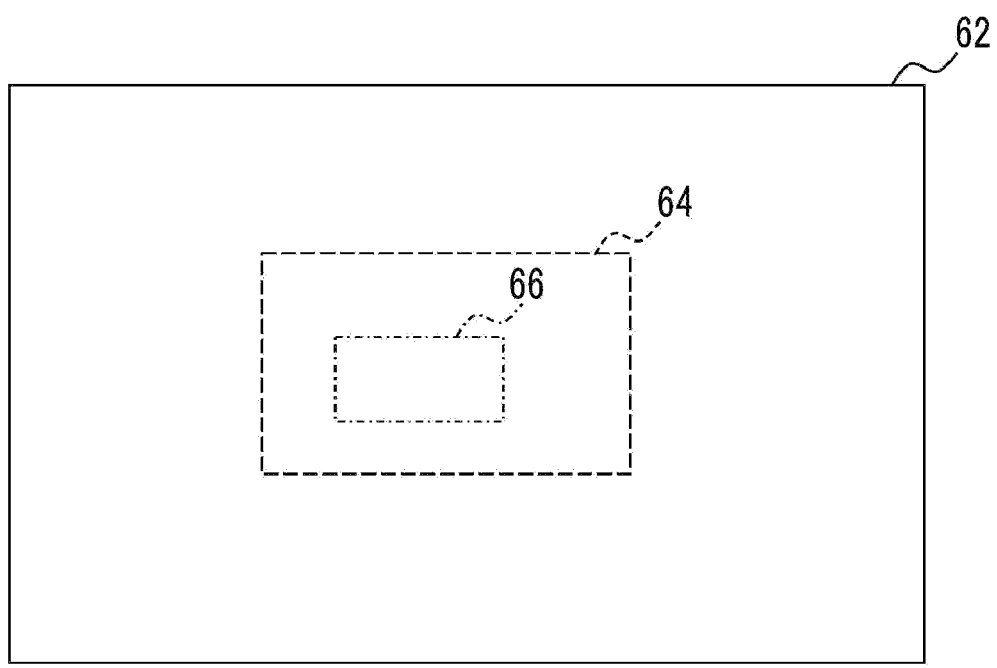
FIG. 9 is a diagram schematically showing a composite image.

FIG. 9 schematically shows a composite image 62. A broken line 64 in FIG. 9 shows an outer periphery of the region of interest, and a one-dot chain line 66 in FIG. 9 shows an outer periphery of the re-measurement region. An outside of the broken line 64 is the B-mode image. An inside of the broken line 64 is the composite image in which the re-measurement image is superimposed on the B-mode elasticity image.

The image combining unit 34 obtains a composite pixel value C by executing a mixing process represented by (Math 1) for each pixel value A of the B-mode elasticity image and each pixel value B of the re-measurement image generated by the re-measurement process.

$$C = (1-\alpha) \cdot A + \alpha \cdot B \qquad \text{(Math 1)}$$

Here, a mixing ratio $\alpha$ indicates a degree at which the pixel value of the re-measurement image contributes to the pixel value of the composite image. A value of the mixing ratio $\alpha$ is decided according to a position in the re-measurement region. That is, the mixing ratio $\alpha$ is a function related to a coordinate value (x, y) of the measurement point P (x, y), and has a value equal to or larger than 1 and equal to or less than 0.

The mixing ratio $\alpha$ may be decided to approach 0 from 1 toward the outer periphery from the centroid of the re-measurement region. In addition, the mixing ratio $\alpha$ may be decided to approach 0 from 1 toward the outside from an inner position by a predetermined distance from the outer periphery of the re-measurement region and to be 0 at the outer periphery.

In addition, the image combining unit 34 may execute a process of superimposing the re-measurement image on a region having the highest degree of approximation to the re-measurement image among the regions on the B-mode elasticity image. Specifically, the image combining unit 34 obtains the correlation value for each position while changing the position of the re-measurement image for the B-mode elasticity image. The image combining unit 34 may execute the mixing process such that a positional relationship between the B-mode elasticity image and the re-measurement image has a positional relationship that maximizes the correlation value.

As described above, the ultrasound diagnostic apparatus 100 comprises the image combining unit 34 that generates the B-mode elasticity image data (ultrasound image data) of the biological tissue based on the SW signal as the measurement signal. The image combining unit 34 generates the composite image data indicating the composite image in which the re-measurement image based on the B-mode elasticity image data generated in the re-measurement of the elastic property is superimposed on a first-measurement image based on the B-mode elasticity image data generated in the first-measurement of the elastic property.

The composite image is an image obtained by performing the mixing process on the first-measurement image and the re-measurement image, and the mixing process is a process of weighting and combining the pixel value of the first-measurement image and the pixel value of the re-measurement image according to the position of the pixel based on (Math 1).

In addition, the image combining unit 34 may deform the re-measurement image such that the degree of approximation between the region on the B-mode elasticity image and the re-measurement image is maximized. The deformation may be performed, for example, by stretching or contracting the re-measurement image in a specific direction. Specifically, the image combining unit 34 obtains the correlation value for the B-mode elasticity image while changing the shape of the re-measurement image. The image combining unit 34 may execute the mixing process after deforming the re-measurement image such that the correlation value is maximized.

Figure 10:
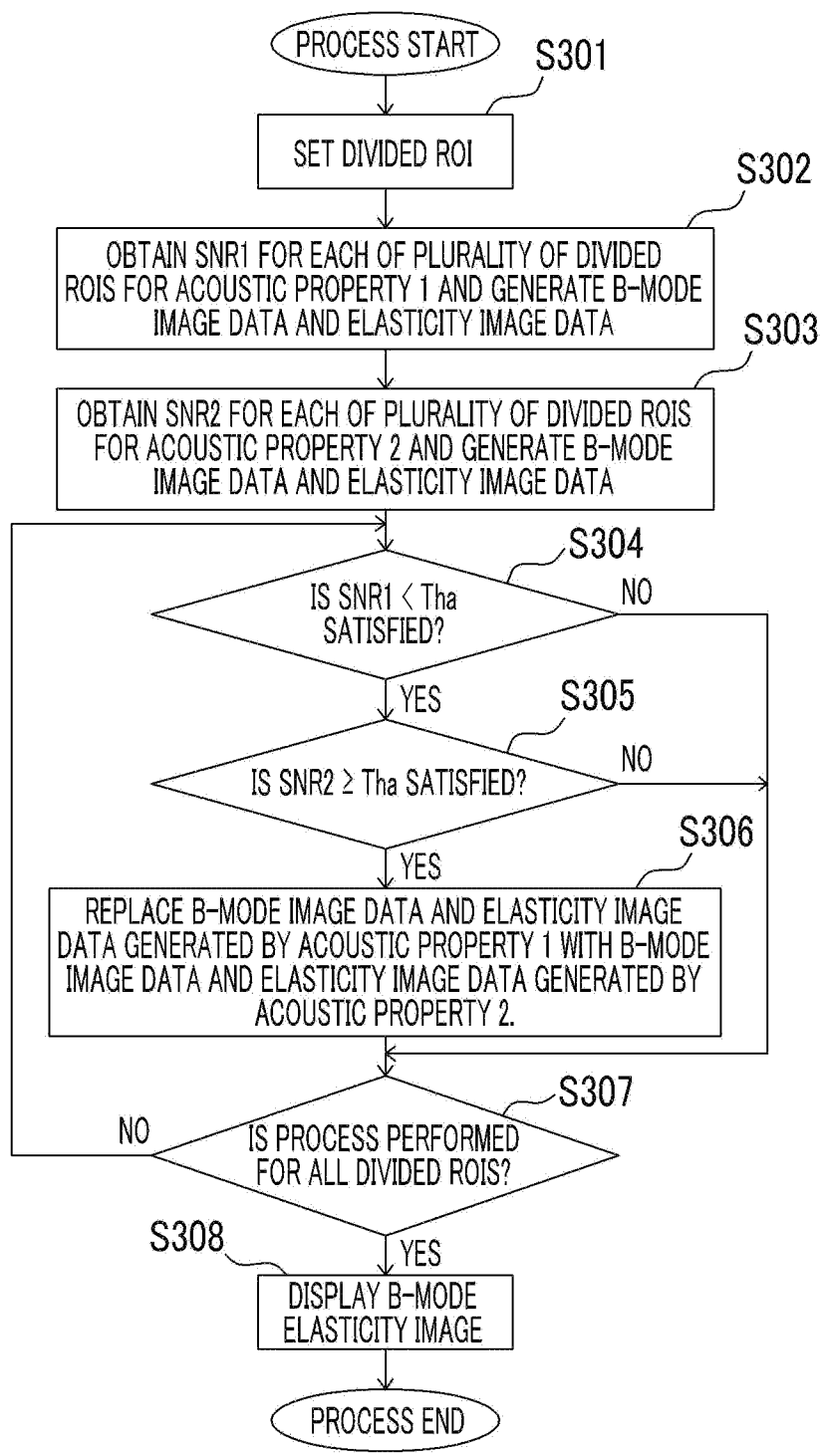
FIG. 10 is a flowchart of a selective measurement process according to an application embodiment.

FIG. 10 shows a flowchart of a selective measurement process according to an application embodiment of the disclosure. In the selective measurement process, the region of interest is divided into a plurality of divided regions of interest, and two types of measurement processes in which the acoustic properties of the push wave are different are executed for each of the divided regions of interest. For each divided region of interest, the measurement result of the acoustic property among two types of the acoustic properties having a better SNR is selected, and the B-mode elasticity image for the entire region of interest is displayed. In the following description, it is assumed that the acoustic properties of the push wave include an acoustic property 1 and an acoustic property 2 in which at least one of the wave train length or the number of times of transmission is different.

The controller 42 divides one region of interest into a plurality of divided regions of interest, and sets a plurality of divided regions of interest (S301). The setting of the divided region of interest is performed, for example, by performing an operation of setting the divided region of interest on the tomographic plane from which the B-mode image is acquired, in a state in which the display processing unit 36 displays the B-mode image on the display 40.

The controller 42 controls the probe drive unit 10, the reception unit 18, and the information processing unit 20, obtains an SNR1 for each of the plurality of divided regions of interest, and causes the information processing unit 20 to generate the B-mode image data and the elasticity image data for each of the plurality of divided regions of interest (S302). Here, the SNR1 refers to the SNR obtained for the acoustic properties 1.

The controller 42 controls the probe drive unit 10, the reception unit 18, and the information processing unit 20, obtains an SNR2 for each of the plurality of divided regions of interest, and causes the information processing unit 20 to generate the B-mode image data and the elasticity image data for each of the plurality of divided regions of interest (S303). Here, the SNR2 refers to the SNR obtained for the acoustic properties 2.

The controller 42 determines whether or not the SNR1 is less than the predetermined threshold value Tha for one divided region of interest that is sequentially selected from among the plurality of divided regions of interest (S304). In a case in which the SNR1 is equal to or larger than the predetermined threshold value Tha, the controller 42 proceeds to the process of step S307. In a case in which the SNR1 is less than the predetermined threshold value Tha, the controller 42 determines whether or not the SNR2 is equal to or larger than the predetermined threshold value Tha (S305). In a case in which the SNR2 is less than the predetermined threshold value Tha, the controller 42 proceeds to the process of step S307. In a case in which SNR2 is equal to or larger than the predetermined threshold value Tha, the controller 42 causes the image combining unit 34 to execute the process of step S306. In step S306, the image combining unit 34 replaces the B-mode image data and the elasticity image data with the B-mode image data and the elasticity image data generated by the acoustic property 2 for the divided regions of interest under the process target.

The controller 42 determines whether or not the processes of steps S304 to S306 are executed for all the divided regions of interest (S307). In a case in which it is determined that the processes of steps S304 to S306 are not executed for all the divided regions of interest, the controller 42 executes the processes of steps S304 to S306 for one divided region of interest next selected from among the plurality of divided regions of interest.

In a case in which it is determined that the processes of steps S304 to S306 are executed for all the divided regions of interest, the controller 42 causes the image combining unit 34 to generate the B-mode elasticity image data based on the B-mode image data and the elasticity image data generated through steps S304 to S306. The display processing unit 36 displays the B-mode elasticity image on the display 40 (S308).

As described above, the controller 42 decides the B-mode image data and the elasticity image data having higher reliability out of the B-mode image data and the elasticity image data (data indicating a first elastic property) obtained for one of a plurality of types of push waves having different acoustic properties and the B-mode image data and the elasticity image data (data indicating a second elastic property) obtained for the other of the plurality of types of push waves, as the B-mode image data and the elasticity image data which are finally obtained (S304 to S306). In the example shown in FIG. 11, the reliability of the B-mode image data and the elasticity image data is determined by whether or not the SNR obtained from the SW signal (measurement signal) is equal to or larger than the threshold value Tha.

With such a process, among the plurality of divided regions of interest, for the divided region of interest in which the SNR1 is less than the predetermined threshold value Tha and the SNR2 is equal to or larger than the predetermined threshold value Tha, the B-mode image data and the elasticity image data acquired for the acoustic property 1 is replaced with the B-mode image data and the elasticity image data acquired for the acoustic property 2. As a result, the B-mode elasticity image with improved visibility is displayed on the display 40.

The reliability of the B-mode image data and the elasticity image data may be determined based on the reflected wave separation degree D obtained for the SW signal (measurement signal). In this case, the following processes may be executed in a case in which the reflected wave separation degree obtained for the acoustic property 1 is denoted by D1 and the reflected wave separation degree obtained for the acoustic property 2 is denoted by D2. That is, among the plurality of divided regions of interest, for the divided region of interest in which the reflected wave separation degree D1 is less than a predetermined threshold value Thd and the reflected wave separation degree D2 is equal to or larger than the predetermined threshold value Thd, the B-mode image data and the elasticity image data acquired for the acoustic property 1 is replaced with the B-mode image data and the elasticity image data acquired for the acoustic property 2.

The ultrasound diagnostic apparatus according to the embodiment of the disclosure may have the following configurations.

Configuration 1

An ultrasound diagnostic apparatus comprising: a push wave transmission unit that transmits a push wave to a biological tissue; a tracking wave transmission/reception unit that transmits a tracking wave to the biological tissue and receives a reflected ultrasound wave that is reflected by the biological tissue; an elasticity analysis unit that measures a propagation velocity of a shear wave generated in the biological tissue by the push wave and measures an elastic property of the biological tissue based on the propagation velocity, the elasticity analysis unit measuring the propagation velocity based on a measurement signal obtained by the reflected ultrasound wave received by the tracking wave transmission/reception unit; and a controller that determines whether or not to re-measure the elastic property according to an unnecessary component included in the measurement signal, in which, in a case in which it is determined to re-measure the elastic property, the ultrasound diagnostic apparatus re-measures the elastic property by changing an acoustic property of the push wave according to the unnecessary component included in the measurement signal.

Configuration 2

The ultrasound diagnostic apparatus according to configuration 1, in which the controller determines whether or not to re-measure the elastic property based on a noise component as the unnecessary component included in the measurement signal.

Configuration 3

The ultrasound diagnostic apparatus according to configuration 1 or 2, in which the controller determines whether or not to re-measure the elastic property based on a reflected wave component as the unnecessary component included in the measurement signal.

Configuration 4

An ultrasound diagnostic apparatus comprising: a push wave transmission unit that transmits a push wave to a biological tissue; a tracking wave transmission/reception unit that transmits a tracking wave to the biological tissue and receives a reflected ultrasound wave that is reflected by the biological tissue; an elasticity analysis unit that measures a propagation velocity of a shear wave generated in the biological tissue by the push wave and measures an elastic property of the biological tissue based on the propagation velocity, the elasticity analysis unit measuring the propagation velocity based on a measurement signal obtained by the reflected ultrasound wave received by the tracking wave transmission/reception unit; and a display processing unit that displays an elasticity image based on the elastic property, in which the ultrasound diagnostic apparatus re-measures the elastic property by changing an acoustic property of the push wave according to an operation of a user performed in a case in which the elasticity image is displayed.

Configuration 5

The ultrasound diagnostic apparatus according to any one of configurations 1 to 4, in which, in a case in which a ratio of magnitude of a shear wave signal component to a noise component included in the measurement signal is less than a predetermined threshold value, in re-measurement, the push wave transmission unit makes a wave train length of the push wave longer than in first-measurement of the elastic property or increases the number of times of transmission of the push wave for each measurement.

Configuration 6

The ultrasound diagnostic apparatus according to any one of configurations 1 to 5, in which, in a case in which a degree of separation between a shear wave signal component and a reflected wave component included in the measurement signal is less than a predetermined threshold value, in re-measurement, the push wave transmission unit makes a wave train length of the push wave shorter than in first-measurement of the elastic property or decreases the number of times of transmission of the push wave for each measurement.

Configuration 7

The ultrasound diagnostic apparatus according to any one of configurations 1 to 6, further comprising: an image combining unit that generates ultrasound image data of the biological tissue based on the measurement signal, and generates composite image data indicating a composite image in which a re-measurement image based on the ultrasound image data generated in re-measurement of the elastic property is superimposed on a first-measurement image based on the ultrasound image data generated in first-measurement of the elastic property, in which the composite image is an image in which a mixing process is performed on the first-measurement image and the re-measurement image, and the mixing process is a process of weighting and combining a pixel value of the first-measure-

Configuration 8

An ultrasound diagnostic apparatus comprising: a push wave transmission unit that transmits a plurality of types of push waves having different acoustic properties to a biological tissue; a tracking wave transmission/reception unit that transmits a tracking wave to the biological tissue and receives a reflected ultrasound wave that is reflected by the biological tissue; an elasticity analysis unit that measures a propagation velocity of a shear wave generated in the biological tissue by the push wave and measures an elastic property of the biological tissue based on the propagation velocity, the elasticity analysis unit measuring the propagation velocity based on a measurement signal obtained by the reflected ultrasound wave received by the tracking wave transmission/reception unit; and a controller that decides an elastic property having higher reliability out of a first elastic property obtained for one of the plurality of types of push waves and a second elastic property obtained for the other of the plurality of types of push waves, as a finally obtained elastic property, in which the reliability is decided based on an unnecessary component included in the measurement signal.

What is claimed is:

1. An ultrasound diagnostic apparatus comprising:
   an ultrasound probe configured to:
   transmit a push wave to a biological tissue; and
   transmit a tracking wave to the biological tissue and receive a reflected ultrasound wave that is reflected by the biological tissue; and
   a processor configured to:
   measure a propagation velocity of a shear wave generated in the biological tissue by the push wave and measure an elastic property of the biological tissue based on the propagation velocity, and measure the propagation velocity based on a measurement signal obtained by the reflected ultrasound wave received by the ultrasound probe; and
   determine whether or not to re-measure the elastic property according to an unnecessary component included in the measurement signal,
   wherein, in a case in which it is determined to re-measure the elastic property, the ultrasound diagnostic apparatus re-measures the elastic property by changing an acoustic property of the push wave according to the unnecessary component included in the measurement signal,
   wherein the processor determines whether or not to re-measure the elastic property based on a noise component as the unnecessary component included in the measurement signal.

2. The ultrasound diagnostic apparatus according to claim 1,
   wherein the processor determines whether or not to re-measure the elastic property based on a reflected wave component as the unnecessary component included in the measurement signal.

3. The ultrasound diagnostic apparatus according to claim 1,
   wherein, in a case in which a ratio of magnitude of a shear wave signal component to the noise component included in the measurement signal is less than a predetermined threshold value, in re-measurement, the ultrasound probe makes a wave train length of the push wave longer than in first-measurement of the elastic property or increases the number of times of transmission of the push wave for each measurement.

4. The ultrasound diagnostic apparatus according to claim 1,
   wherein, in a case in which a degree of separation between a shear wave signal component and a reflected wave component included in the measurement signal is less than a predetermined threshold value, in re-measurement, the ultrasound probe makes a wave train length of the push wave shorter than in first-measurement of the elastic property or decreases the number of times of transmission of the push wave for each measurement.

5. The ultrasound diagnostic apparatus according to claim 1,
   wherein the processor is further configured to:
   generate ultrasound image data of the biological tissue based on the measurement signal, and
   generate composite image data indicating a composite image in which a re-measurement image based on the ultrasound image data generated in re-measurement of the elastic property is superimposed on a first-measurement image based on the ultrasound image data generated in first-measurement of the elastic property,
   wherein the composite image is an image in which a mixing process is performed on the first-measurement image and the re-measurement image, and
   the mixing process is a process of weighting and combining a pixel value of the first-measurement image and a pixel value of the re-measurement image according to a position of a pixel.

6. An ultrasound diagnostic apparatus comprising:
   an ultrasound probe configured to:
   transmit a push wave to a biological tissue; and
   transmit a tracking wave to the biological tissue and receive a reflected ultrasound wave that is reflected by the biological tissue; and
   a processor configured to:
   measure a propagation velocity of a shear wave generated in the biological tissue by the push wave and measure an elastic property of the biological tissue based on the propagation velocity, and measure the propagation velocity based on a measurement signal obtained by the reflected ultrasound wave received by the ultrasound probe; and
   display an elasticity image based on the elastic property,
   wherein the ultrasound diagnostic apparatus re-measures the elastic property by changing an acoustic property of the push wave according to an operation of a user performed in a case in which the elasticity image is displayed,
   wherein the processor determines whether or not to re-measure the elastic property based on a noise component as the unnecessary component included in the measurement signal.

7. The ultrasound diagnostic apparatus according to claim 6,
   wherein, in a case in which a ratio of magnitude of a shear wave signal component to the noise component included in the measurement signal is less than a predetermined threshold value, in re-measurement, the ultrasound probe makes a wave train length of the push wave longer than in first-measurement of the elastic property or increases the number of times of transmission of the push wave for each measurement.

8. The ultrasound diagnostic apparatus according to claim 6,
wherein, in a case in which a degree of separation between a shear wave signal component and a reflected wave component included in the measurement signal is less than a predetermined threshold value, in re-measurement, the ultrasound probe makes a wave train length of the push wave shorter than in first-measurement of the elastic property or decreases the number of times of transmission of the push wave for each measurement.

9. The ultrasound diagnostic apparatus according to claim 6,
wherein the processor is further configured to:
generate ultrasound image data of the biological tissue based on the measurement signal, and
generate composite image data indicating a composite image in which a re-measurement image based on the ultrasound image data generated in re-measurement of the elastic property is superimposed on a first-measurement image based on the ultrasound image data generated in first-measurement of the elastic property,
wherein the composite image is an image in which a mixing process is performed on the first-measurement image and the re-measurement image, and
the mixing process is a process of weighting and combining a pixel value of the first-measurement image and a pixel value of the re-measurement image according to a position of a pixel.

10. An ultrasound diagnostic apparatus comprising:
an ultrasound probe configured to:
transmit a plurality of types of push waves having different acoustic properties to a biological tissue; and
transmit a tracking wave to the biological tissue and receive a reflected ultrasound wave that is reflected by the biological tissue; and
a processor configured to:
measure a propagation velocity of a shear wave generated in the biological tissue by the push wave and measure an elastic property of the biological tissue based on the propagation velocity, and measure the propagation velocity based on a measurement signal obtained by the reflected ultrasound wave received by the ultrasound probe; and
decide an elastic property having higher reliability out of a first elastic property obtained for one of the plurality of types of push waves and a second elastic property obtained for the other of the plurality of types of push waves, as a finally obtained elastic property,
wherein the reliability is decided based on an unnecessary component included in the measurement signal,
wherein the processor determines whether or not to re-measure the elastic property based on a noise component as the unnecessary component included in the measurement signal.

* * * * *